US006713583B2

(12) United States Patent
Liao et al.

(10) Patent No.: US 6,713,583 B2
(45) Date of Patent: Mar. 30, 2004

(54) INTRAOCULAR LENSES MADE FROM POLYMERIC COMPOSITIONS

(75) Inventors: Xiugao Liao, Irvine, CA (US); Joseph I. Weinschenk, III, Fortworth, TX (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 113 days.

(21) Appl. No.: 09/792,841

(22) Filed: Feb. 23, 2001

(65) Prior Publication Data

US 2001/0005743 A1 Jun. 28, 2001

Related U.S. Application Data

(62) Division of application No. 09/265,720, filed on Mar. 9, 1999, now Pat. No. 6,241,766.
(60) Provisional application No. 60/106,381, filed on Oct. 29, 1998.

(51) Int. Cl.[7] ............................ C08F 118/02; A61F 2/16
(52) U.S. Cl. ................ 526/319; 526/303.1; 526/307.1; 526/318; 526/318.1; 526/318.44; 526/320; 526/329.2; 623/6.11; 623/6.56
(58) Field of Search .................... 526/264, 303.1, 526/328.5, 347, 307.1, 318, 318.1, 318.3, 318.4, 318.44, 319, 320, 329.2; 623/6.11, 6.56

(56) References Cited

U.S. PATENT DOCUMENTS

| | | | |
|---|---|---|---|
| 4,834,750 A | | 5/1989 | Gupta |
| 5,290,892 A | * | 3/1994 | Namdaran et al. .......... 526/259 |
| 5,331,073 A | * | 7/1994 | Weinschenk et al. ....... 526/264 |
| 5,359,021 A | * | 10/1994 | Weinschenk et al. ....... 526/264 |
| 5,429,703 A | | 7/1995 | Hartman et al. |
| 5,603,774 A | * | 2/1997 | LeBoeuf et al. ................ 134/1 |
| 5,674,960 A | * | 10/1997 | Namdaran et al. .......... 526/259 |
| 5,814,680 A | * | 9/1998 | Imafuku et al. ............. 523/106 |
| 5,861,031 A | | 1/1999 | Namdaran et al. |

FOREIGN PATENT DOCUMENTS

| | | |
|---|---|---|
| EP | 0514096 | 11/1992 |
| EP | 657751 | 6/1995 |
| EP | 0811393 | 10/1997 |
| EP | 0811393 | 12/1997 |
| WO | 9411764 | 5/1994 |
| WO | 9425510 | 11/1994 |
| WO | 9908136 | 2/1999 |

OTHER PUBLICATIONS

Hoya Corp., Publication No. 08308921, Japanese Abstract.
Okamoto, Chemical Abstracts, vol. 95, No. 8, Aug. 24, 1981, Abstract No. 62812.
Ohe, Chemical Abstracts, vol. 121, No. 4, Jul. 25, 1994, Abstract No. 46389.

* cited by examiner

*Primary Examiner*—Tatyana Zalukaeva
(74) *Attorney, Agent, or Firm*—Stout, Uxa, Buyan & Mullins, LLP; Frank J. Uxa; Peter J. Gluck

(57) ABSTRACT

Ophthalmic lenses, such as intraocular lenses, include cross-linked polymeric materials having a first constituent derived from a first monomeric component selected from the group consisting of acrylates, methacrylates and mixtures thereof, and a second constituent derived from a second component in an amount effective as a cross linker in the cross-linked polymeric material. The cross-linked polymeric material has branched chain alkyl groups, preferably included with at least a portion of the first monomeric component, in an amount effective to reduce the tackiness of the cross-linked polymeric material relative to a substantially identical cross-linked polymeric material without the branched chain alkyl groups.

12 Claims, 1 Drawing Sheet ically cut in the eye than for the implantation of "hard" IOLs
INTRAOCULAR LENSES MADE FROM POLYMERIC COMPOSITIONS

CROSS REFERENCE TO RELATED APPLICATION

This application is a division of application Ser. No. 09/265,720, filed Mar. 9, 1999, now U.S. Pat. No. 6,241,766, which claimed the benefit of provisional application Ser. No. 60/106,381 filed Oct. 29, 1998, the entire disclosure of each of which is hereby incorporated by reference herein.

BACKGROUND OF THE INVENTION

The present invention relates to ophthalmic lenses made from polymeric compositions. More particularly, the invention relates to ophthalmic lenses, preferably deformable intraocular lenses, having reduced surface tackiness made from acrylate and/or methacrylate-based polymeric compositions.

Intraocular lenses (IOLs) have been known for a long time, since shortly after the end of World War II. Such a lens is surgically implanted into a mammalian eye, e.g., human eye, to replace a damaged or diseased natural lens of the eye and restore the patient's vision.

Although IOLs are made from "hard" or "rigid" polymeric or glass optical materials, such as polymethyl methacrylate (which has a refractive index of 1.49), soft resilient polymeric materials, such as silicones, have been increasingly used, for the reasons discussed below, in ophthalmic applications.

Since soft IOLs are deformable, for example, foldable or rollable, for implantation, a smaller incision can be surgically cut in the eye than for the implantation of "hard" IOLs of the same optical power. The smaller the incision, the less trauma the patient's eye experiences and the faster post-operative healing occurs. An incision of about 3 mm is ideal since this size incision is presently required to remove the natural lens after it has been broken up, for example, emulsified in a conventional phaceoemulsification procedure. In contrast the typical IOL optic has a diameter of about 6 mm.

The size and mechanical characteristics of the deformable IOLs play an important role. As is well understood by those skilled in the art, for successful implantation, the deformable IOL must have sufficient structural integrity, elasticity and elongation and be small enough in size to permit deforming for insertion through a small incision. After insertion, the lens must, of course, regain its original shape and have sufficient structural integrity to retain such shape under normal use conditions.

In general, the thinner the deformable IOL the smaller the incision in the eye that is required. On the other hand, in order to function optically as an IOL, the lens must have sufficient optical refractory power. Also, the higher the optical refractive index of the material making up the IOL, the thinner the IOL can be and still obtain the same optical refractory power.

Deformable IOLs made of acrylic materials can be quite tacky in nature, which tackiness inhibits deforming to a sufficiently small size for insertion through a very small incision and/or may cause handling problems Gupta U.S. Pat. No. 4,834,750 discloses IOLs with optics made of copolymers of methacrylate esters which form homopolymers that are relatively hard at room temperature and acrylate esters which form homopolymers that are relatively soft at room temperature. Such copolymers are cross-linked with a diacrylate ester to produce an acrylate material which preferably includes a constituent derived from a fluoroacrylate to reduce surface tackiness. None of the specific monomers disclosed in this patent provide homopolymers which have a refractive index of at least about 1.50.

Weinschenk, III U.S. Pat. No. 5,331,073 discloses acrylic-based intraocular lenses which optionally include a constituent derived from a hydrophilic monomeric component. This constituent is effective to reduce the tackiness of the copolymer. However, such hydrophilic constituent may cause a disadvantageous decrease in the index of refraction of the final IOL optic in that some water is included within the copolymer.

LeBoeuf et al U.S. Pat. No. 5,603,774 discloses plasma treatment of the polymer surface to reduce tackiness associated with certain acrylic polymers, particularly those polymers useful in intraocular lenses. However, such plasma treatment does involve an additional manufacturing step. Also, the non-homogeneous intraocular lens which results from the surface being treated with plasma has the potential of causing problems in the eye.

It would be advantageous to provide ophthalmic lens materials of construction which have good optical properties, including optical clarity and high refractive index (index of refraction) and, in addition, have reduced tackiness without the disadvantages of the prior art materials noted above.

SUMMARY OF THE INVENTION

New polymeric materials and ophthalmic lenses, for example, IOLs, produced from such polymeric materials have been discovered. The present polymeric materials are derived from a combination of monomers and provide very useful optical properties in terms of optical clarity and high index of refraction and can be formed into ophthalmic lenses, for example, optics of IOLs which are effectively deformable, preferably foldable, for insertion through small surgical incisions, preferably on the order of about 3 mm or less (in maximum transverse dimension). Importantly, the present compositions and ophthalmic lenses have reduced surface tackiness without requiring the presence of fluoroacrylates, hydrophilic components and without requiring plasma treatment. By selecting the monomeric components used to produce the present compositions and ophthalmic lenses in accordance with the present invention, reduced surface tackiness is achieved with little or no adverse impact on the optical clarity, refractive index, homogeneity, biocompatability, deformability, and cost of production of such compositions and ophthalmic lenses. The present compositions and lenses can be produced using conventional techniques, e.g., conventional polymerization techniques. Thus, the present invention is very effective and easy to practice and results in polymeric compositions and ophthalmic lenses which have outstanding properties.

In one broad aspect of the present invention, ophthalmic lens bodies are provided which comprise cross-linked polymeric materials or compositions. Such materials comprise a first constituent derived from a first monomeric component selected from acrylates, methacrylates and mixtures thereof. A second constituent is included and is derived from a second component in an amount effective as a cross linker in the cross-linked polymeric material. The cross-linked polymeric material has branched chain alkyl groups in an amount effective to reduce the tackiness of the cross-linked polymeric material relative to a substantially identical crosslinked polymeric material without the branched chain alkyl groups. It has been found that the inclusion of branched chain alkyl groups, for example, in the first monomeric component, or portion thereof, unexpectedly provides reduced surface tackiness to the cross-linked polymeric material. Thus, this reduced tackiness is obtained without requiring the presence of a fluoroacrylate or a hydrophilic component and without requiring treating, for example, plasma treating, the surface of the polymeric material.

The present ophthalmic lens bodies may be in the form of optics of IOLs, contact lenses, corneal implants (for example, corneal onlays and corneal inlays) and other ophthalmic lens bodies. The present lens bodies are particularly useful as optics of IOLs, more preferably deformable IOLs. Because a deformable IOL is adapted to be deformed, that is rolled, folded or otherwise deformed, prior to insertion into the eye, it is important that the IOL optic have a relatively reduced degree of surface tackiness to provide for effective deforming for insertion and/or to allow the optic to effectively regain its original shape in the eye.

The term "branched chain alkyl groups", as used herein, refers to alkyl groups which are non-linear. Thus, at least one, and preferably more than one, carbon atom in the alkyl group is located in one or more branches, rather than being located in a single linear portion of the alkyl group. Also, cycloalkyl groups are, by definition, branched chain alkyl groups. The branched chain alkyl group may be of any size suitable to function as described herein. Preferably, the branched chain alkyl group has about 3 to about 20 carbon atoms and more preferably about 6 to about 15 carbon atoms.

The amount of branched chain alkyl groups present is sufficient to provide a cross-linked polymeric material having reduced tackiness relative to a substantially identical cross-linked polymeric material without the branched chain alkyl groups. The monomeric component, for example, the first monomeric component, or portion thereof, including the branched chain alkyl groups used in providing the present cross-linked polymeric materials may represent a wide ranging proportion of the total monomeric components employed. Preferably, the branched chain alkyl group-containing monomeric component, or portion thereof, provides a constituent of the cross-linked polymeric materials which is present in an amount in the range of about 1% or less to about 50% or more, and more preferably about 3% to about 25%, by weight of the cross-linked polymeric material.

The first monomeric component, or at least a portion thereof, preferably is selected from acrylates including a branched chain alkyl group, methacrylates including a branched chain alkyl group and mixtures thereof. In one useful embodiment, the cross-linked polymeric material includes a third constituent derived from a third monomeric component other than the first and second monomeric components. This third monomeric component is selected from acrylates, methacrylates and mixtures thereof. Preferably, the first monomeric component is selected from acrylates having a branched chain alkyl group and mixtures thereof. The third monomeric component preferably is selected from methacrylates and mixtures thereof.

In one embodiment the present cross-linked polymeric material has reduced tackiness relative to a substantially identical cross-linked polymeric material in which the first constituent is replaced by a constituent derived from a monomeric component having a straight chain alkyl group having the same number of carbon atoms as the branched chain alkyl groups of the first monomeric component.

Advantageously, the cross-linked polymeric material has an index of refraction of at least about 1.50. Relatively high indexes of refraction allow the ophthalmic lenses, and in particular IOLs, to be conveniently manufactured with relatively high optical powers and the capability of being passed through scleral tunnel incisions of about 3.0 mm or even about 2.8 mm or less. Preferably, the cross-linked polymeric material includes aryl-containing groups in an amount effective to increase the index of refraction of the cross-linked polymeric material relative to the index of refraction of a substantially identical cross-linked polymeric material without the aryl-containing groups. In a very useful embodiment, the third monomeric component includes an effective amount of aryl-containing groups to increase the index of refraction of the cross-linked polymeric material, as desired.

In order to provide the desired degree of deformability, the cross-linked polymeric material preferably has a glass transition temperature (Tg) of about 22° C. or less. Thus, in the context of an IOL optic, a cross-linked polymeric material having a Tg within this preferred range can be folded or otherwise deformed for insertion at or about room temperature.

Each individual feature and each combination of two or more features described herein are included within the scope of the present invention provided that the features included in the combination are not mutually inconsistent.

These and other aspects of the present invention are set forth in the following detailed description, examples and claims, particularly when considered in conjunction with the accompanying drawings in which like parts bear like reference numerals.

DETAILED DESCRIPTION OF THE INVENTION

Figure 1:
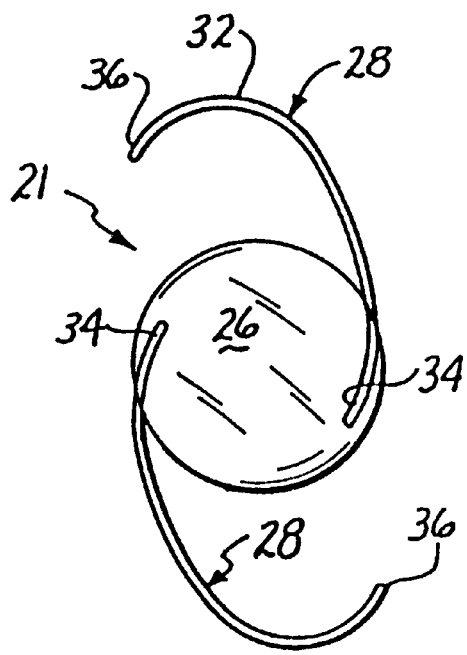
FIG. 1 is a plan view of an IOL in accordance with the present invention.

The present ophthalmic lens bodies comprise cross-linked polymeric materials as described herein. Such cross-linked polymeric materials comprise a combination of constituents derived from different monomeric components. Thus, the present cross-linked polymeric materials comprise a first constituent and a second constituent, and preferably a third constituent.

The first constituent of the present cross-linked polymeric materials is derived from a first monomeric component selected from the group consisting of acrylates, methacrylates and mixtures thereof. At least a portion of the first monomeric component preferably is selected from acrylates including a branched chain alkyl group, methacrylates including a branched chain alkyl group and mixtures thereof.

The present cross-linked polymeric materials have branched chain alkyl groups in an amount effective to reduce the tackiness of the cross-linked polymeric materials relative to a substantially identical cross-linked polymeric materials without the branched chain alkyl groups. When, as is preferred, the first monomeric component, or portion thereof, includes branched chain alkyl groups, such first monomeric component, or portion thereof, is preferably present in an amount to provide an effective tackiness reducing amount of the branched chain alkyl groups.

The branched chain alkyl group-containing monomeric component, for example, the first monomeric component, or portion thereof, preferably provides a constituent of the cross-linked polymeric material which is present in an amount in the range of about 1% or less to about 50% or more, more preferably about 3% to about 25% by weight, of the total cross-linked polymeric material.

Homopolymers of the first monomeric component preferably have a Tg of less than about 30° C., more preferably less than about 22° C.

Typical examples of the first monomeric component include, but are not limited to 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

The second constituent of the present cross-linked polymeric materials is derived from a second monomeric component in an amount effective as a crosslinker in the present cross-linked polymeric materials. This second monomeric component preferably is multi-functional and can chemically react with the first monomeric component, and more preferably with both the first and third monomeric components. The second constituent of the present cross-linked polymeric materials is present in an amount effective to provide a desired degree of shape memory to the materials, for example, to facilitate returning a deformed IOL made from the present cross-linked polymeric material to its original shape, for example, in a reasonable period of time, at the conditions present in the human eye.

The second or cross linking monomeric component is often present in a minor amount relative to the amounts of the first and third monomeric components. Preferably, the second constituent is present in the cross-linked polymeric material in an amount of less than about 1% by weight of the material. The second constituent of the present cross-linked polymeric materials may be considered to be a cross linker. The cross linking monomeric component is often selected from multi functional components, preferably able to chemically react with at least one functional group of each of the first monomeric component and the third monomeric component. The cross linking monomeric component is chosen to be chemically reactable with at least one functional group associated with one or both of the first monomeric component and the third monomeric component.

Examples of the second monomeric component for use in the present cross-linked polymeric materials include, but are not limited to, ethylene glycol dimethacrylate, tetraethylene glycol dimethacrylate, allyl acrylate, allyl methacrylate, trifunctional acrylates, trifunctional methacrylates, tetrafunctional acrylates, tetrafunctional methacrylates and mixtures thereof.

The third monomeric component used in producing the cross-linked polymeric materials of the present invention is different from the first and second monomeric components. Such third monomeric component is selected from acrylates, methacrylates and mixtures thereof. The third constituent of the present cross-linked polymeric materials preferably is present to provide a constituent of the cross-linked polymeric material in an amount of at least about 10% or about 20% by weight, and more preferably in a major amount (at least about 50%) by weight, of the cross-linked polymeric material. In one very useful embodiment, the third constituent is derived from a third monomeric component the homopolymers of which have an index of refraction of at least about 1.50, preferably at least about 1.52 or about 1.54. The homopolymers of the third monomeric component may have a substantial degree of rigidity.

In one particularly useful embodiment, the first and third constituents together are preferably at least about 80%, more preferably at least about 90%, by weight of the present cross-linked polymeric materials. The first and third monomeric components preferably are selected so that each of these monomeric components can chemically react with the other monomeric component.

The present cross-linked polymeric materials have reduced surface tackiness and preferably are optically clear and have high indexes of refraction, for example, at least about 1.50, and preferably at least about 1.52 or at least about 1.54. The combination of properties of the present cross-linked polymeric materials, for example, which facilitates the manufacture of effectively deformable IOLs having high optical power, is very advantageous.

As used herein, the term "homopolymer" refers to a polymer which is derived substantially completely from the monomeric component in question. Thus, such homopolymer includes as the primary, preferably sole, monomeric component, the monomeric component in question. Minor amounts of catalysts, initiators and the like may be included, as is conventionally the case, in order to facilitate the formation of the homopolymer. In addition, the homopolymers of both the first monomeric component and the third monomeric component have sufficiently high molecular weights or degrees of polymerization so as to be useful as IOL materials of construction.

The homopolymers of the third monomeric component may be rigid. An IOL made from such a "rigid" homopolymer is not deformable, for example, using systems which are specifically structured and used to deform IOLs for insertion through a small incision into the eye. The rigidity of the homopolymer of the third monomeric constituent may result in an IOL made from such homopolymer being not deformable, or breaking or otherwise deteriorating as a result of the application of force seeking to so deform such IOL for implantation through a small ocular incision.

The third constituent preferably is present in an amount of at least about 10% or at least about 20%, more preferably in a major amount, by weight of the present cross-linked polymeric materials. The third monomeric component from which the third constituent is derived may be selected from compounds which meet the criteria set forth herein for such component. This monomeric component preferably is such as to provide the present cross-linked polymeric materials with increased refractive index relative to the homopolymers of the first monomeric component. The homopolymers of the third monomeric component preferably have an index of refraction of at least about 1.50, and more preferably at least about 1.52 or at least about 1.54.

In one embodiment, the third monomeric component is characterized as including one or more aryl-containing groups. Without wishing to limit the present invention to any particular theory of operation, it is believed that the presence of such aryl-containing groups in the third monomeric component at least facilitates, and preferably leads to or results in, the present cross-linked polymeric materials having desirably high refractive indexes. If the third monomeric component includes one or more aryl-containing groups, it is preferred that at least the first monomeric component, and more preferably that the first and second monomeric components, include no aryl-containing groups. This "single index of refraction control" is very effective in achieving high index of refraction cross-linked polymeric materials, and allows flexibility in selecting the other monomeric component or components so that cross-linked polymeric materials with advantageous properties, other than index of refraction, for example, cross-linked polymeric materials formable into IOLs which can be effectively deformed (for insertion) at room temperature, can be obtained.

Examples of the third monomeric component which may be included in the present cross-linked polymeric materials include, but are not limited to, benzyl acrylate, benzyl methacrylate, phenyl acrylate, phenyl methacrylate, phenoxyalkyl acrylates, phenoxyalkyl methacrylates, phenylalkyl acrylates, phenylalkyl methacrylates, carbazole acrylates, carbazole methacrylates, biphenyl acrylates, biphenyl methacrylates, naphthyl acrylates, naphthyl methacrylates and mixtures thereof.

Of course, the first, second and third monomeric components should be such as to provide cross-linked polymeric materials which are compatible for use in or on the eye, are optically clear and are otherwise suitable for use as materials of construction for ophthalmic lenses. In one useful embodiment, each of the first, second and third monomeric components is substantially free of silicon, so that the resulting copolymer is not a silicone polymer. The monomeric components may be substituted with substantially non-interfering substituents which have a substantial detrimental effect on the cross-linked polymeric materials produced therefrom. Such substituents may include one or more elements, such as oxygen, nitrogen, carbon, hydrogen, halogen, sulfur, phosphorus, and the like and mixtures and combinations thereof.

The cross-linked polymeric materials of the present invention preferably have glass transition temperatures (Tg) of about 22° C. or less. Such glass transition temperatures (Tg) are beneficial in facilitating the deforming (folding) of an IOL the optic of which is made of an embodiment of the present cross-linked polymeric material at room temperature prior to inserting the IOL through a small incision into the eye.

The present cross-linked polymeric materials may be produced using conventional polymerization techniques. For example, the monomers can be blended together, cast into the form of a sheet, and heated to an elevated temperature, such as in a range of about 50° C. to about 90° C. for a period of time in a range of about 30 minutes to about 8 hours or about 24 hours or more, to facilitate the polymerization reaction. Catalysts and/or initiators, for example, selected from materials well known for such use in the polymerization art, may be included in the monomer mix in order to promote, and/or increase the rate of, the polymerization reaction. Examples of such initiators include 2,2'-azobis (2,4-dimethylpentanenitrile), 2,2'-azobis (2-methylpropanenitrile), 2,2'-azobis (2-methylbutanenitrile), peroxides such as benzoyl peroxide, UV initiators such as diethoxyacetophenone, and the like and mixtures thereof.

In addition, effective amounts of ultraviolet light absorbing monomeric components, such as functional benzotriazole and benzophenone derivatives, may be included in the precursor monomer mix. Such UV light absorbing monomeric components are polymerized into the final cross-linked polymeric material to provide the final material with effective UV light absorbing properties.

In one particularly useful embodiment, the present cross-linked polymeric materials are produced by mixing together the first monomeric component and the third monomeric component. This mixture is well blended, deareated and heated to a temperature, for example, of about 50° C. to about 80° C. and maintained at this temperature for a period of time, for example, of about 15 minutes to about 3 hours. The mixture undergoes partial polymerization to form a viscous liquid when cooled to about 25° C.

The final cross-linked polymeric materials can be produced by combining this partially polymerized viscous liquid, the second or cross linking monomeric component and catalyst and/or an initiator. Alternately, all the monomeric components and catalyst and/or initiator can be combined or mixed together. The viscous liquid, or monomeric mixture, is well blended, deareated and poured into a mold. The mold is heated, preferably to a temperature of about 40° C. to about 100° C., and the liquid or mixture is allowed to cure, preferably for about 1 hour to about 24 hours. The material in the mold is then post-cured, preferably at a temperature in the range of about 70° C. to about 130° C., for a period of time, preferably for about 2 to about 30 hours. After curing (and post-curing), the mold is disassembled and the molded lens body recovered.

Alternately, the curing and post-curing occurs in a tube. The cross-linked polymeric material formed in the tube is cut into cylindrical lens blanks. The lens blanks can be machined to produce the finished lens body, e.g., IOL optic. Such machining may involve milling and lathing at cryogenic temperatures.

Figure 2:
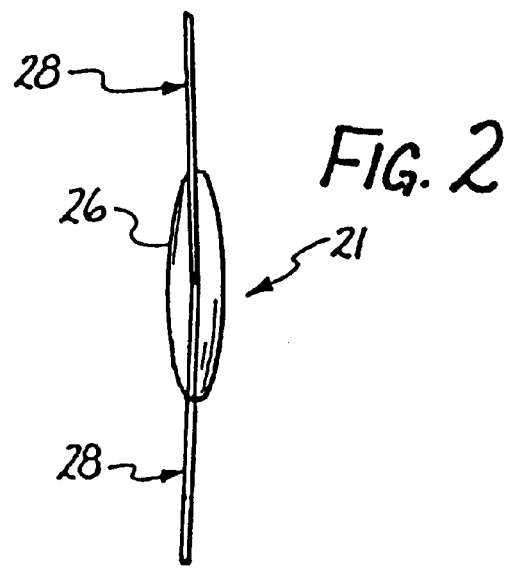
FIG. 2 is a side view of the IOL of FIG. 1.

Referring now to FIGS. 1 and 2, IOL 21 is illustrated as including a pair of radially outwardly extending haptics or fixation members 28 secured to optically clear optic 26. Alternately, the optic and fixation members can be formed from a single piece of material. Each haptic 28 has a substantially uniform cross section throughout its length and is shown provided with a smoothly curved region 32, intermediate a lens bonding region 34 and a free end region 36. Although the illustrated embodiment is provided with two opposing haptics 28, it is understood that an IOL having only one haptic or more than two haptics bonded to the optic is within the scope of the invention.

Optic 26 is made of a cross-linked polymeric material in accordance with the present invention, for example, the material as set forth in Example 1 hereof. Optic 26 can be formed in accordance with conventional IOL optic forming techniques, such as by injection molding, sheet casting and cutting to form bottons and the like techniques. Alternately, the monomeric components can be first mixed in a tube and then cured in the tube. The resulting rod then is cut into buttons which are then cryolathed into IOL optics.

Typically, each haptic 28 comprises a flexible member comprising metal or, preferably, polymeric material, and having a substantially circular cross-section, although alternative cross-sectional configurations may be substituted, if desired. Although the haptics may take on any suitable configuration, the illustrated haptics 28 are relatively thin and flexible, while at the same time being sufficiently strong to provide support for IOL 21 in eye 10. The haptics 28 may comprise any of a variety of materials which exhibit sufficient supporting strength and resilience, and which are substantially biologically inert in the intended in vivo environment. Suitable materials for this purpose include, for example, polymeric materials such as polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitonal, and the like. The haptics can be produced using conventional and well known forming techniques. For example, the preferred polymeric haptics can be formed in accordance with known thermoplastic polymer forming techniques, such as by injection molding or by extrusion.

The lens bonding regions 34 of the haptics 28, which, as described herein, are secured to optic, may be provided with any of a variety of configurations, such as an anchoring loop, an anchoring "T", or other anchor structure, to provide a mechanical interlock with the optic, such as has been done in the prior art.

IOL 26 can be formed using any one of various techniques, such as those conventionally used to form IOLs. For example, the lens bonding regions 34 of haptics 28 can be placed in a mold which is filled with a mix of the monomeric components used to form the optic 26. The mold is then subjected to conditions, e.g., elevated temperature, effective to form the cross-linked polymeric materials of the present invention from this monomer mix. The lens bonding regions 34 become bonded to the optic 26, thereby securing the haptics 28 to the optic. Alternately, the haptics 28 can be secured in recesses provided in the already formed optic 26.

Optic 26 has low or reduced surface tackiness, and preferably an index of refraction of at least about 1.50. Optic 26 is foldable for insertion into a human eye through an incision of about 3 mm in length. After insertion into the eye in the folded condition, IOL 21 returns to its original shape in a reasonable period of time, for example, on the order of about 1 second or about 20 seconds to about three minutes, and can be easily positioned in the eye for effective and long term use as a replacement for the natural lens normally present in the eye.

The following non-limiting examples illustrate certain aspects of the present invention.

EXAMPLE 1

The following formulation is blended, purged with nitrogen for 3 minutes and then cured into a cross-linked copolymer.

|  | Weight % |
| --- | --- |
| 2-Phenoxyethyl acrylate | 32.5 |
| 2-Phenoxyethyl methacrylate | 48.7 |
| 3,5,5-trimethylhexyl acrylate | 14.7 |
| Ethylene glycol dimethacrylate | 2.0 |
| Ultraviolet light absorbing Monomeric component [1] | 2.0 |
| Radical initiator [2] | 0.11 |

[1] 2-(4-benzoyl-4-hydroxyphenoxy)ethylacrylate
[2] 2,5-dimethyl-2,5-bis(2-ethylhexanoylperoxy)hexane The resulting cross-linked copolymer has an index of refraction of 1.54, a glass transition temperature (Tg) of 15° C., excellent optical transparency (clarity) and good mechanical properties, including low or reduced tackiness. A one cm diameter rod of this copolymer is folded 180° with no cracking and returns to its original shape within a few seconds at 35° C.

EXAMPLE 2

Using conventional techniques, an optic is formed from the crosslinked copolymer produced in Example 1. In order to produce a 20 diopter, plano-convex optic, having a 0.305 mm edge thickness and a 6.0 mm diameter, the optic center thickness is approximately 0.737 mm.

EXAMPLE 3

An IOL is produced having an optic as indicated in Example 2. Two substantially opposing haptics, such as shown in FIGS. 1 and 2, made from extruded poly methyl methacrylate filaments are bonded to this optic. The resulting IOL is inserted into the eye through a 3 mm surgical incision. In order to accomplish such insertion, the IOL is folded. Upon being released into the eye, the IOL regains its original shape in less than one minute and is fixed in position in the eye. After normal healing, the IOL is effective and useful in the eye as a replacement for the natural lens normally present in the eye.

EXAMPLE 4

The cross-linked polymer of Example 1 (Example 1 Copolymer) and a cross-linked copolymer similar to the cross-linked copolymer produced in Example 1 (Example 4 Copolymer) are made or cast in the form of sheets. Both copolymers are made in a manner similar to how the copolymer of Example 1 is made. The composition of the Example 4 Copolymer is similar to the copolymer of Example 1 except that n-nonyl acrylate is used in place of 3,5,5-trimethylhexyl acrylate.

A series of discs shaped and sized similar to optics of intraocular lenses are produced from each of these sheets. A lens folding forceps is used to fold these discs in half (180°). After holding the folded disc in the forceps for 30 seconds, the disc is released from the forceps into a beaker containing water at 35° C. The amount of time required for the disc to release from itself, referred to as the "tack time", is recorded. Also, the amount of time required of the disc to return to flatness or its original shape, referred to as the "unfold time", is recorded.

Results of these tests are as follows:

| Disc | Material | Tack Time, seconds | Unfold Time, seconds |
| --- | --- | --- | --- |
| 1 | Example 1 Copolymer | 19 | 35 |
| 2 | Example 1 Copolymer | 17 | 44 |
| 3 | Example 1 Copolymer | 12 | 34 |
| 4 | Example 1 Copolymer | 11 | 33 |
| 5 | Example 1 Copolymer | 26 | 46 |
|  | AVERAGE | 17 | 38 |
| 6 | Example 4 Copolymer | 33 | 41 |
| 7 | Example 4 Copolymer | 32 | 42 |
| 8 | Example 4 Copolymer | 51 | 62 |
| 9 | Example 4 Copolymer | 34 | 45 |
| 10 | Example 4 Copolymer | 23 | 33 |
|  | AVERAGE | 35 | 45 |

These results demonstrate that the Example 1 Copolymer has reduced tackiness relative to the Example 4 Copolymer. Since substantially the only difference in these two materials is the presence of a monomer including a branched chain alkyl group, that is 3,5,5-trimethylhexyl acrylate, in the Example 1 Copolymer, these results make clear that this type of monomer is surprisingly effective in advantageously reducing the tackiness of cross-linked copolymers derived from such monomers, and in particular ophthalmic lenses including such copolymers.

While this invention has been described with respect to various specific examples and embodiments, it is to be understood that the invention is not limited thereto and that it can be variously practiced within the scope of the following claims.

What is claimed is:

1. A composition comprising a cross-linked polymeric material comprising a first constituent derived from a first monomeric component selected from the group consisting of acrylates having a branched chain alkyl group, methacrylates having a branched chain alkyl group and mixtures thereof, a second constituent derived from a second monomeric component in an amount effective as a cross linker in the cross-linked polymeric material and a third constituent derived from a third monomeric component, number of carbon atoms as the branched chain alkyl group of the first monomeric component.

2. The composition of claim 1 wherein the third monomeric component includes an aryl-containing group, and the cross-linked polymeric material has an index of refraction of at least about 1.50.

3. The composition of claim 1 wherein the first monomeric component is selected from a group consisting of acrylates having a branched chain alkyl group and mixtures thereof and the third monomeric component is selected from a group consisting of methacrylates and mixtures thereof.

4. The composition of claim 1 wherein the branched chain alkyl groups are selected from a class consisting of alkyl groups having 3 to about 20 carbon atoms and mixtures thereof.

5. The composition of claim 1 wherein the branded chain alkyl groups are selected from a class consisting of alkyl groups having about 6 to about 15 carbon atoms and mixtures thereof.

6. The composition of claim 1 wherein the cross-linked polymeric material includes aryl-containing groups in an amount effective to increase the index of refraction of the cross-linked polymeric material relative to the index of refraction of a substantially identical cross-linked polymeric material without the aryl-containing groups.

7. The composition of claim 1 wherein the cross-linked polymeric material has a glass transition temperature of about 22° C. or less.

8. The composition of claim 1 which is substantially homogeneous.

9. The composition of claim 1 wherein the cross-linked polymeric material is substantially free of hydrophilic groups effective to reduce the tackiness of the cross-linked polymeric material.

10. The composition of claim 1 wherein at least a portion of the first monomeric component is selected from a group consisting of 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

11. The composition of claim 1 wherein the second monomeric component is selected from a group consisting of tetraethylene glycol dimethacrylate, alkyl acrylate, alkyl methacrylate, trifunctional acrylates, trifunctional methacrylates, tetrafunctional acrylates, tetrafunctional methacrylates and mixtures thereof.

12. The composition of claim 1 wherein the third monomeric component is selected from a group consisting of benzyl acrylate, benzyl methacrylate, phenyl acrylate, phenyl methacrylate, phenoxy alkyl acrylates, phenoxy alkyl methacrylates, carbazole acrylates, carbazole methacrylates, biphenyl acrylates, biphenyl methacrylates, naphthyl acrylates, naphthyl methacrylates and mixtures thereof.

* * * * *

UNITED STATES PATENT AND TRADEMARK OFFICE
CERTIFICATE OF CORRECTION

PATENT NO.   : 6,713,583 B2
DATED        : March 30, 2004
INVENTOR(S)  : Xiugao Liao and Joseph I. Weinschenk, III It is certified that error appears in the above-identified patent and that said Letters Patent is hereby corrected as shown below:

<u>Column 10,</u>
Claim 1, should read as follows:
   1. A composition comprising a cross-linked polymeric material comprising a first constituent derived from a first monomeric component selected from the group consisting of acrylates having a branched chain alkyl group, methacrylates having a branched chain alkyl group and mixtures thereof, a second constituent derived from a second monomeric component in an amount effective as a cross linker in the cross-linked polymeric material and a third constituent derived from a third monomeric component, other than the first and second monomeric components, selected from the group consisting of acrylates, methacrylates and mixtures thereof, the cross-linked polymeric material having branched chain alkyl groups form the first monomeric component in an amount effective to provide reduced tackiness relative to a substantially identical cross-linked polymeric material in which the first constituent is replaced by a constituent derived from a monomeric component having a straight chain alkyl group having the same number of carbon atoms as the branched chain alkyl group of the first monomeric component.

Signed and Sealed this

Eighth Day of June, 2004

JON W. DUDAS
*Acting Director of the United States Patent and Trademark Office*